United States Patent [19]
Kim et al.

[11] Patent Number: 5,457,039
[45] Date of Patent: Oct. 10, 1995

[54] METHOD FOR HYPER-PRODUCTION OF MONASCUS PIGMENTS

[75] Inventors: Jun-Sung Kim; Kee-Hyun Choi, both of Seoul; Jang-Youn Choi, Kyungki-do; Yoon-Soo Lee; Ik-Boo Kwon, both of Seoul, all of Rep. of Korea

[73] Assignee: Lotte Confectionery Co., Ltd., Seoul, Rep. of Korea

[21] Appl. No.: 119,344

[22] Filed: Sep. 9, 1993

[30] Foreign Application Priority Data

Oct. 26, 1992 [KR] Rep. of Korea ............. 92-19730

[51] Int. Cl.$^6$ ................. C12N 1/20; C12P 17/18
[52] U.S. Cl. ..................... 435/119; 435/254.1
[58] Field of Search ................. 435/254.1, 119

[56] References Cited

U.S. PATENT DOCUMENTS

| | | | |
|---|---|---|---|
| 3,765,906 | 11/1973 | Yamaguchi | 435/119 |
| 4,442,209 | 4/1984 | Miyake | 435/119 |

OTHER PUBLICATIONS

Jae-Ho Lee, Kee-Hyun Choi, Jang-Youn Choi, Yoon-Soo Lee, Ik-Kwon and Ju-Hyun Y, "Enzymatic production of α-cyclodextrin with the cyclomaltodextrin glucanotransferase of Klebsiella oxytoca 19-1", *Enzyme and Microbial Technology botechnology Research and Reviews*, Dec. 1992, vol. 14, No. 12, Raymond E. Spier and Sheldon W. May, Editors, pp. 1017–1020.

Kim, Jun–Sung. Kee–Hyun Choi, Jang–Yoon Choi, Yoon–Soo Lee, Young–Youl Chang and Ik–Boo Kwon, "Induction of a Mutant, Monascus anka 732Y3 from Monascus anka KFCC 11832 and its Morphological Observations", *Journal of Microbiology and Biotechnology*. Jun. 1993, vol. 3, No. 2, pp. 134–138.

*Primary Examiner*—Irene Marx
*Attorney, Agent, or Firm*—Kenyon & Kenyon

[57] ABSTRACT

The present invention relates to a method for producing high amounts of Monascus pigment by cultivating a Monascus species in a particularly prepared media to which rice powder and peptone are added as carbon and nitrogen sources, respectively.

5 Claims, No Drawings

METHOD FOR HYPER-PRODUCTION OF MONASCUS PIGMENTS

BACKGROUND OF THE INVENTION

1. Field of the Invention

The present invention relates to a method for producing high amounts of Monascus pigment by cultivating a Monascus species in particularly prepared media to which rice powder and peptone are added as carbon and nitrogen sources, respectively.

2. Description of the Related Art

Nowadays, with increasing doubts about the health safety of artificial pigments many researchers have begun to search for safe pigments to take the place of them, especially, natural pigments. Among artificial pigments, those permitted for use in developed countries like America and Japan are only a few, and the amounts of them added to food are also restricted. Among many natural pigments which come from animals, plants, and microorganisms, microbial pigments appear to be the most promising from the viewpoints of how to apply the pigments, how to produce them, and how to cultivate the producers.

Monascus sp., a fungus, which traditionally has been used in countries like China and Japan for the fermentative production of red wine and red soybean cheese, attracted great interest with respect to ease of approach.

The pigments comprising the Monascus color are rubropunctatin ($C_{21}H_{22}O_5$-red color), monascorubrin($C_{23}H_{26}O_5$-red color), monascin($C_{21}H_{26}O_5$-yellow color), ankaflavin($C_{23}H_{30}O_5$)-yellow color, rubropunctamine($C_{21}H_{23}NO_4$-purple color), and monascorubramine($C_{23}H_{27}NO_4$-purple color) (Y. C. Su, Kor. J. Appl. Microbiol. Bieng., 11, 325, 1983).

Tadao Hiroi made it clear by his test that a Monasous species produces none of aflatoxin $B_1$, $B_2$, $G_1$, and $G_2$. And also, from the reversion plate test, it was not observed that the pigments work as frame shift mutagens. Rec-assay with *Bacillus subtilis* H-17 and M-45, in addition, confirmed the negative effect of the pigments on DNA-destruction. Furthermore, rats fed on the pigments were reported not to be harmed (H, Tadao, New Food Industry, 30, 1, 1988).

The proof that the Monascus pigments are safe to health brought many researchers including Hiroi to efforts to produce high amounts of them. They have, as often as not, pointed out that attention must be paid to the compositions of the media, above all, to nitrogen sources. According to the study of Carel and Shepherd, an oxidized nitrogen increases the yield of the purple pigments, that is, rubropunctamine and monascorubramine, and a reduced nitrogen increases that of the red pigments such as rubropunctatin and monascorubrin. It is also said that organized nitrogens are very effective for the growth of Monascus species while not effective for high production of the pigments. A nitrate stimulates asexual propagation followed by conidiation, and an ammounium stimulates sexual propagation accompanied by the formation of cleistothecia(M. Carel and D. Shepherd, Can. & Microbiol., 23, 1360, 1977). If the above report by Su that the production of Monascus pigments increases by inhibition of conidiation is considered, it will not be favorable to the production of the pigments to cultivate the Monascus sp. in a medium containing a nitrate. Therefore, it is believed that high production of Monascus pigments will assured if a Monascus sp. propagates sexually more often than asexually, if a reduced nitrogen is contained in the medium used, and if suitable growth is guaranteed.

SUMMARY OF THE INVENTION

The objective of this invention is to produce high amounts of Monascus pigments by cultivating a Monascus species in a particular carbon and nitrogen source-added medium. An embodiment comprises culturing a Monascus species in media containing 5–11% of rice powder. A specific embodiment comprises cultivation of a Monascus species in a media containing 0.1% of various forms of nitrogen. A still more specific embodiment comprises cultivation of a Monascus species in media containing 0.1~1.0% of peptone as the nitrogen source. Other embodiments will be apparent from the following description

DESCRIPTION OF THE INVENTION

The observation that forms the basis of this invention is the production of high amounts of Monascus pigments by cultivating a Monascus species in particularly prepared media to which rice powder and peptone are added as carbon and nitrogen sources, respectively. The Monascus strains used for this invention were *Monascus anka* ATCC 16360 (=IFO 4478, KFCC 11832), *Monascus purpureus* Went KFCC 35473 (= IFO 4513, ATCC 16365), and *Monascus anka* KCCM 10014. The latter strain, which is newly induced from *Monascus anka* KCCM 10014. The latter strain, which is newly induced from *Monascus anka* ATCC 16360 by the inventors, has been deposited with the Korea Culture Center of Microorganisms through International Depositary Authority on Aug. 18, 1992, given an accession number of KCCM-10014.

Compared with those of its parental strain, *M. Anka* ATCC 16360, the cultural, physiological, and morphological characteristics of *M. anka* 732Y3 (KCCM 10014) are represented in Tables 1, 2, 3-1 and 3-2.

TABLE 1

Cultural Characteristics of *M. anka* ATCC 16360 and its Mutant, *M. anka* 732Y3 (KCCM 10014)

| Medium | Temp. (°C.) | *M. anka* ATCC 16360 | *M. anka* 732Y3 (KCCM 10014) |
|---|---|---|---|
| CYA | 25 | colony size: 24–28 mm | colony size: 19–21 mm |

TABLE 1-continued

Cultural Characteristics of M. anka ATCC 16360 and its Mutant, M. anka 732Y3 (KCCM 10014)

| Medium | Temp. (°C.) | M. anka ATCC 16360 | M. anka 732Y3 (KCCM 10014) |
|---|---|---|---|
| | | colony shape: round shape; bright pink; short mycelia | colony shape: round shape; red; short mycelia |
| | 37 | colony size: 35–44 mm | colony size: 20–30 mm |
| | | colony shape: round shape; very bright pink; very numerous short mycelia | colony shape: shapeless; dark red; a few short mycelia |
| MEA | 25 | colony size: 13–18 mm | colony size: 9–15 mm |
| | | colony shape: shapeless; yellow; long mycelia | colony shape: shapeless; orange; only a few mycelia |
| | 37 | colony size: 20–28 mm | colony size: 4–15 mm |
| | | colony shape: shapeless; yellow; long mycelia | colony shape: shapeless; orange; only a few mycelia |
| G25N | 25 | colony size: 23–27 mm | colony size: 17–22 mm |
| | | colony shape: round shape; very bright pink; very neumerous mycelia | colony shape: round shape; red; short mycelia |
| | 37 | colony size: 38–45 mm | colony size: 16–21 mm |
| | | colony shape: round shape; red; very numerous short mycelia | colony shape: shapeless; dark red; only a few mycelia |

TABLE 2

Physiological Characteristics of Monascus anka ATCC 16360 and its Mutant, Monascus anka 732Y3 (KCCM 10014)

| Hydrolysis | M. anka ATCC 16360 | M. anka 732Y3 (KCCM 10014) |
|---|---|---|
| starch hydrolysis | ++ | ++ |
| fat hydrolysis | + | + |
| gelatin hydrolysis | + | + |
| casein hydrolysis | + | + |
| urea hydrolysis | +− | +− |

−: poorly done
+: well done
media: The compositions of the media used were those of Czapek Yeast Agar except sucrose, which was replaced by starch, olive oil for tat, gelatin, casein, or urea.
duration of culture : 7 days

TABLE 3-1

Morphological Characteristics of Monascus anka ATCC 16360 and its Mutant, Monascus anka 732Y3 (KCCM 10014)

| Organ | M. anka ATCC 16360 | M. anka 732Y3 (KCCM 10014) |
|---|---|---|
| hypha | + | + |
| septum | + | + |
| ascospore | + | + |
| cleistothecium | + | + |
| conidiospore | + | + |
| oidium | − | − |
| coremium | − | − |
| rhizoid | − | − |
| zygospore | − | − |
| sporangiospore | − | − |

+: existent
−: non-existent

TABLE 3-2

Morphological Characteristics of Monascus anka ATCC 16360 and its Mutant, Monascus anka 732Y3 (KCCM 10014)

| | Organ | M. anka ATCC 16360 | M. anka 732Y3 (KCCM 10014) |
|---|---|---|---|
| quantity | cleistothecia | ++ | +++ |
| | conidia | ++++ | ++ |
| size (μm) | cleistothecium | 37.0–75.0 | 85.0–107.0 |
| | ascospore | 2.5–4.0 | 2.5–5.8 |
| | conidium | 10.0–25.0 | 15.0–22.5 |

+ to ++++: a few to many
medium: potato dextrose agar(20% infusion from potato, 2% dextrose, 1.5% agar)
temperature: 30° C.
incubation peroid: 7 days
pH: 4.5

Although, as revealed in Table 2 and 3-1, the above two strains, Monascus anka ATCC 16360 and Monascus anka 732Y3 (KCCM 10014), have physiological characteristics similar to each other, they have different cultural and morphological characteristics. Above all, if the morphological characteristics am examined, it can be seen that the development of conidia of the mutant, Monascus anka 732Y3 (KCCM 10014), is less extensive than that of Monascus anka ATCC 16360.

Furthermore, the microscopic observation of Monascus anka 732Y3 (KCCM 10014) represented more active sexual propagation than its parental strain, which can be suggested by the larger and more numerous cleistothecia than those of Monascus anka ATCC 16360.

The above Monascus strains were subcultured onto slant media of 5 ml containing 10% sucrose, 0.1% $KH_2PO_4$, 0.05% $MgSO_4 \cdot 7H_2O$, 0.2% $NaNO_3$, 0.05% KCl, 0.001% $FeSO_4 \cdot 7H_2O$, 0.3% yeast extract, 0.5% casamino acid, and 2.0% agar powder. After 7 days incubation at 30° C., these strains were inoculated in pigment production media containing 5~11% rice powder as carbon source, 0.1% various nitrogen sources, 0.01% $MgSO_4 \cdot 7H_2O$, and 0.25% $KH_2PO_4$. The above concentrations of $MgSO_4 \cdot 7H_2O$ and $KH_2PO_4$ were chosen at random for the supply of minerals. The pigments were extracted with 95% ethanol.

7% rice powder was found out to be the most effective as the carbon source. In case of the nitrogen source, an organic nitrogen source, as long as its concentration is as low as 0.1%, is preferable for both of growth and pigment production to an inorganic nitrogen source.

0.1~1.0% peptone was very effective from the in viewpoints of the yields of the pigments and the growth of the Monascus strains. In particular, 0.3% peptone had the most outstanding effect on the pigment production. But, these results refute the comments of Carel and Shepherd's. According to the their comments, an organic nitrogen was said to only stimulate the growth. The experiments of the inventors also showed consistent results as theirs in that organic nitrogens, on the whole, facilitate the growth of the Monascus strains, but that this effect did not consist only of growth but also of pigmentation unless the concentration of an organic nitrogen could be otherwise controlled. This phenomenon suggests that the pigments are related to the growth of the Monascus strains.

Monascus pigments, which are safe to health, stable, and economical, can be applied to dyestuffs in the food industry in place of artificial dyestuffs.

The following Examples are presented to illustrate this invention and should not be regarded as limiting it any way.

EXAMPLE 1

*Monascus purpureus* Went KFCC 35473, *Monascus anka* ATCC 16360(=IFO 4478, KFCC 11832), *Monasous anka* KCCM 10014 were subcultured at 30° C. for 7 days in the media containing 10% sucrose, 0.1% $KH_2PO_4$, 0.05% $MgSO_4 \cdot 7H_2O$, 0.2% $NaNO_3$, 0.05% KCl, 0.001% $FeSO_4 \cdot 7H_2O$, 0.3% yeast extract, 0.5% casamino acid, and 2.0% agar. And these subcultured Monascus strains were inoculated into media containing 5, 7, 9 or 11% rice powder, 0.15% $NaNO_3$ as nitrogen source, 0.1% $MgSO_4 \cdot 7H_2O$, and 0.25% $KH_2PO_4$, and then, cultured at 30° C. with a reciprocal stroke of 120 rpm for 7 days. When the cultivation was over, 200 ml of 95% ethanol was added for extraction of the pigments. The extracts were filtered through filter paper of No. 2. The optical densities of the filtrates were detected at 500 nm and 400 nm for red and yellow pigments, respectively.

The results of the tests are set forth in Table 4 below.

TABLE 4

Pigment Production by Monascus Strains in Media of Various Concentrations of Rice Powder

| Strains | % of rice powder | Pigments produced 500 nm (red) | Pigments produced 400 nm (yellow) | Dry cell weight (mg/50 ml) |
|---|---|---|---|---|
| M. purpureus Went KFCC 35473 | 5 | 1.06 | 1.13 | 582 |
| | 7 | 1.27 | 1.81 | 818 |
| | 9 | 1.13 | 1.40 | 993 |
| | 11 | 0.95 | 1.17 | 1260 |
| M. anka ATCC 16360 | 5 | 6.02 | 6.39 | 625 |
| | 7 | 7.84 | 9.02 | 873 |
| | 9 | 7.09 | 7.83 | 1059 |
| | 11 | 5.82 | 6.45 | 1484 |
| M. anka | 5 | 44.0 | 50.6 | 538 |

TABLE 4-continued

Pigment Production by Monascus Strains in Media of Various Concentrations of Rice Powder

| Strains | % of rice powder | Pigments produced 500 nm (red) | Pigments produced 400 nm (yellow) | Dry cell weight (mg/50 ml) |
|---|---|---|---|---|
| KCCM 10014 | 7 | 56.8 | 58.1 | 701 |
| | 9 | 46.3 | 53.0 | 1006 |
| | 11 | 30.7 | 33.5 | 1181 |

EXAMPLE 2

The Monascus strains were subcultured and cultured in the same way as in EXAMPLE 1 in a media containing 7% rice powder, the concentration which was selected to be the most preferable in the experiment of EXAMPLE 1, 0.1% various nitrogen sources, 0.1% $MgSO_4 \cdot 7H_2O$, and 0.25% $KH_2PO_4$. Among the various nitrogen sources, peptone was proved to be the most effective, and the results of the test are set forth in Table 5.

TABLE 5

Pigment Production by Monascus Strains in Media with 0.1% of Various Nitrogen Sources

| Strains | Nitrogen sources | Pigments produced 500 nm (red) | Pigments produced 400 nm (yellow) | Dry cell weight (mg/50 ml) |
|---|---|---|---|---|
| M. purpureus Went KFCC 35473 | none | 0.35 | 0.48 | 755 |
| | $NaNO_3$ | 1.32 | 1.84 | 810 |
| | $NH_4Cl$ | 1.17 | 0.95 | 691 |
| | $NH_4NO_3$ | 1.56 | 1.44 | 912 |
| | $KNO_3$ | 0.89 | 0.93 | 905 |
| | $KNO_2$ | 0.71 | 0.96 | 823 |
| | glycine | 1.43 | 1.92 | 930 |
| | MSG | 0.74 | 0.96 | 823 |
| | yeast extract | 1.81 | 1.92 | 987 |
| | casamino acid | 1.85 | 1.87 | 925 |
| | peptone | 2.11 | 2.04 | 866 |
| | polypeptone | 1.78 | 2.00 | 950 |
| | urea | 0.45 | 0.63 | 943 |
| M. anka ATCC 16360 | none | 1.53 | 2.76 | 760 |
| | $NaNO_3$ | 6.12 | 9.63 | 880 |
| | $NH_4Cl$ | 6.03 | 8.66 | 701 |
| | $NH_4NO_3$ | 7.00 | 7.07 | 904 |
| | $KNO_3$ | 5.53 | 6.00 | 916 |
| | $KNO_2$ | 5.68 | 5.81 | 856 |
| | glycine | 6.89 | 7.33 | 963 |
| | MSG | 3.04 | 3.58 | 718 |
| | yeast extract | 8.25 | 8.62 | 1005 |
| | casamino acid | 9.01 | 10.14 | 999 |
| | peptone | 13.96 | 15.32 | 905 |
| | polypeptone | 9.40 | 10.25 | 1000 |
| | urea | 1.84 | 1.79 | 991 |
| M. anka KCCM 10014 | none | 16.0 | 10.4 | 500 |
| | $NaNO_3$ | 60.3 | 62.7 | 697 |
| | $NH_4Cl$ | 58.9 | 42.7 | 478 |
| | $NH_4NO_3$ | 65.0 | 53.4 | 800 |
| | $KNO_3$ | 48.6 | 42.0 | 863 |
| | $KNO_2$ | 32.5 | 30.9 | 673 |
| | glycine | 62.6 | 59.3 | 847 |
| | MSG | 37.2 | 34.1 | 383 |
| | yeast extract | 78.3 | 69.7 | 927 |
| | casamino acid | 80.8 | 67.9 | 847 |
| | peptone | 94.7 | 74.3 | 717 |
| | polypeptone | 81.4 | 75.0 | 850 |
| | urea | 18.8 | 17.2 | 880 |

MSG: monosodium glutamate

EXAMPLE 3

Monascus stains were subcultured and cultured in the same way as in EXAMPLE 1, and the media used in this test were composed of 7% rice powder, 0.1% $MgSO_4 \cdot 7H_2O$, 0.25% $KH_2PO_4$, and 0.1~1.0% peptone, which by the experiments of EXAMPLE 2, proved to be preferable to any other nitrogen source. Results are presented in Table 6.

TABLE 6

Effect of the Concentrations of Peptone

| Strains | Peptone, % | Pigments produced 500 nm (red) | 400 nm (yellow) | Dry cell weight (mg/50 ml) |
|---|---|---|---|---|
| M. purpureus Went KFCC 35473 | 0.1 | 1.89 | 1.94 | 871 |
| | 0.2 | 2.55 | 2.76 | 906 |
| | 0.3 | 3.00 | 3.26 | 960 |
| | 0.4 | 2.80 | 2.94 | 1004 |
| | 0.5 | 1.91 | 2.00 | 1302 |
| | 1.0 | 0.66 | 0.87 | 1591 |
| M. anka ATCC 16360 | 0.1 | 11.9 | 12.3 | 992 |
| | 0.2 | 14.1 | 14.0 | 980 |
| | 0.3 | 16.1 | 17.5 | 1103 |
| | 0.4 | 12.0 | 13.8 | 1199 |
| | 0.5 | 7.5 | 8.2 | 1320 |
| | 1.0 | 5.4 | 6.3 | 1454 |
| M. anka KCCM 10014 | 0.1 | 99 | 73 | 756 |
| | 0.2 | 116 | 86 | 811 |
| | 0.3 | 157 | 148 | 955 |
| | 0.4 | 100 | 80 | 975 |
| | 0.5 | 69 | 63 | 1110 |
| | 1.0 | 45 | 42 | 1240 |

EXAMPLE 4

Monascus pigments produced by Monascus strains cultured in Lin's medium and the medium set up in the experiments of EXAMPLES 1, 2, and 3 were tested to see the effect of the new medium: the former is composed of 3% rice powder, 0.15% sodium nitrate, 0.1% magnesium sulfate, heptahydrate, and 0.25% potassium phosphate, monobasic, and the latter consists of 0.7% rice powder, 0.3% peptone, 0.1% magnesium sulfate heptahydrate, and 0.25% potassium phosphate, monobasic.

The results are presented in Table 7.

TABLE 7

Pigment Production by Monascus Strains in Two Different Media

| Strains | Media | Pigments produced 500 nm (red) | 400 nm (yellow) | Dry cell weight (mg/50 ml) |
|---|---|---|---|---|
| M. purpureus Went KFCC 35473 | A | 0.86 | 0.92 | 345 |
| | B | 4.47 | 4.09 | 951 |
| M. anka ATCC 16360 | A | 4.55 | 7.06 | 350 |
| | B | 14.8 | 12.1 | 1014 |
| M. anka KCCM 10014 | A | 29.0 | 32.7 | 337 |
| | B | 152 | 146 | 968 |

A: 3% rice powder, 0.15% $NaNO_3$, 0.1% $MGSO_4 \cdot 7H_2O$, 0.25% $KH_2PO_4$
B: 7% rice powder, 0.3% peptone, 0.1% $MgSO_4 \cdot 7H_2O$, 0.25% $KH_2PO_4$ The results of this experiment demonstrates that 5~7% rice powder and 0.1~ 1.0% peptone, when used as carbon and nitrogen sources, greatly increase pigment production by Monascus species, regardless of its species. Peptone, notwithstanding the fact that is an organic nitrogen source, is significantly effective with respect to Monascus pigment production.

What is claimed is:

1. A method for producing pigments by cultivation of *Monascus anka* KCCM 10014 comprising:
   providing a culture medium consisting essentially of between about 5 and 11% rice powder and between about 0.1 and 1.0% peptone;
   growing said *Monascus anka* KCCM 10014 in said culture medium; and
   recovering said pigments.

2. A method according to claim 1 in which said culture medium consists essentially of between about 5 and 9% rice powder and between about 0.1 and 1.0% peptone.

3. A method according to claim 1 in which said culture medium consists essentially of between about 5 and 7% rice powder and between about 0.1 and 1.0% peptone.

4. A method according to claim 1 in which said culture medium consists essentially of between about 5 and 11% rice powder and between about 0.1 and 0.5% peptone.

5. A method for producing pigments by cultivation of *Monascus anka* KCCM 10014 comprising:
   providing a culture medium consisting essentially of between about 5 and 7% rice powder and between about 0.1 and 0.5% peptone;
   growing said *Monascus anka* KCCM 10014 in said culture medium; and
   recovering said pigments.

* * * * *

UNITED STATES PATENT AND TRADEMARK OFFICE
CERTIFICATE OF CORRECTION

PATENT NO. : 5,457,039                            Page 1 of 5
DATED : 10 October 1995
INVENTOR(S) : Jun-Sung KIM et al.

It is certified that error appears in the above-identified patent and that said Letters Patent is hereby corrected as shown below:

| Column | Line | |
|---|---|---|
| 1 | 16 | After "pigments" insert --,--. |
| 1 | 40 | Change "Monasous" to --Monascus--. |
| 2 | 15 | After "will" insert --be--. |
| 2 | 45 | Delete "The latter strain, which is newly". |
| 2 | 46 | Delete "induced from *Monascus anka* KCCM 10014." |
| 2 | 50 | Before "given" insert --and--. |

UNITED STATES PATENT AND TRADEMARK OFFICE
CERTIFICATE OF CORRECTION

PATENT NO. : 5,457,039
DATED : 10 October 1995
INVENTOR(S) : Jun-Sung KIM et al.

It is certified that error appears in the above-identified patent and that said Letters Patent is hereby corrected as shown below:

| Column | Line | |
|---|---|---|
| 2 | 51 | After "KCCM-10014." insert the following: --The taxonomic classification of this strain is as follows: Kingdom: Monera; Phylum: Eumycota; Sub-division: Ascomycotina; Class: Plectomycetes; Order: Eurotialcs; Family: Aspergillaceae; Genus: *Monascus*; Species: *Anka*. The address of the Korean Culture Center of Microorganisms is as follows: Department of Food Engineering, College of Engineering, Yonsei University, Sodaemun-gu, Seoul 120-749 Korea.--. |

UNITED STATES PATENT AND TRADEMARK OFFICE
CERTIFICATE OF CORRECTION

PATENT NO. : 5,457,039

DATED : 10 October 1995

INVENTOR(S) : Jun-Sung KIM et al.

*It is certified that error appears in the above-identified patent and that said Letters Patent is hereby corrected as shown below:*

| Column | Line |
|---|---|
| 3 | Table I, line 6 from bottom line: Change "neumerous" to --numerous--. |
| 3 | After Table I, delete "0" and insert the following: | duration of culture : 7 days

CYA : Czapek Yeast Agar (pH 7.1) : 0.3% $NaNO_3$, 0.1% $KH_2PO_4$, 0.05% KCl, 0.05% $MgSO_4 \cdot 7H_2O$, 0.01% $FeSO_4 \cdot 7H_2O$, 0.5% yeast extract, 3.0% sucrose, 1.5% agar MEA : Malt Extract Agar(pH 5.6) : 2% malt extract, 0.1% peptone, 2% glucose, 1.5% agar G25N : Glycerol 25% Nitrate Agar(pH 7.1) : 0.3% $NaNO_3$, 0.1% $KH_2PO_4$, 0.05% KCl, 0.01% $MgSO_4 \cdot 7H_2O$, 0.01% $FeSO_4 \cdot 7H_2O$, 0.5% yeast extract, 2.5% glycerol, 1.5% agar

UNITED STATES PATENT AND TRADEMARK OFFICE
CERTIFICATE OF CORRECTION

PATENT NO. : 5,457,039

DATED : 10 October 1995

INVENTOR(S) : Jun-Sung KIM et al.

It is certified that error appears in the above-identified patent and that said Letters Patent is hereby corrected as shown below:

| Column | Line | |
|---|---|---|
| 3 | 41 | Change "+—" to -- + - -- (2 occurrences). |
| 3 | 45 | Change "tat" to --fat--. |
| 4 | 52 | Change "am" to --are--. |
| 5 | 5 | Delete "out". |
| 5 | 8 | Change "for both of" to --both for--. |
| 5 | 10 | Before "view-" delete "in". |
| 5 | 17 | Delete "as theirs". |
| 5 | 29 | After "it" insert --in--. |
| 5 | 34 | After "11832)," insert --and--; change "Monasous" to --Monascus--. |
| 5 | 35 | After "in" delete "the". |

UNITED STATES PATENT AND TRADEMARK OFFICE
CERTIFICATE OF CORRECTION

PATENT NO. : 5,457,039
DATED : 10 October 1995
INVENTOR(S) : Jun-Sung KIM et al.

It is certified that error appears in the above-identified patent and that said Letters Patent is hereby corrected as shown below:

| Column | Line |  |
|--------|------|--|
| 5 | 45 | After "paper" delete "of". |
| 6 | 17 | Before "Monascus" delete "The". |
| 7 | 5-8 | Adjust and conform typeface. |
| 8 | 23 | After "that" insert --it--. |

Signed and Sealed this

Seventeenth Day of December, 1996

BRUCE LEHMAN

*Attesting Officer*   *Commissioner of Patents and Trademarks*